United States Patent [19]

Kaetsu et al.

[11] Patent Number: 4,582,719

[45] Date of Patent: Apr. 15, 1986

[54] PROCESS FOR PRODUCING A SLOW RELEASE COMPOSITE

[75] Inventors: Isao Kaetsu; Masaharu Asano; Minoru Kumakura; Masaru Yoshida, all of Gunma, Japan

[73] Assignee: Japan Atomic Energy Research Institute, Tokyo, Japan

[21] Appl. No.: 514,026

[22] Filed: Jul. 15, 1983

Related U.S. Application Data

[63] Continuation-in-part of Ser. No. 233,084, Feb. 10, 1981, abandoned.

[30] Foreign Application Priority Data

Feb. 13, 1980 [JP] Japan .................................. 55-16405
Feb. 19, 1980 [JP] Japan .................................. 55-19420
May 28, 1980 [JP] Japan .................................. 55-71046

[51] Int. Cl.$^4$ .......................... A01N 1/01; B01J 19/12; B05D 3/06
[52] U.S. Cl. .................... 427/2; 204/157.68; 424/19; 427/53.1; 427/54.1; 427/44; 524/704; 264/4.33; 264/4.7
[58] Field of Search ........ 204/158 R, 158 HE, 158 N, 204/158 S, 159.12; 424/36, 37, 359, 19; 427/2, 53.1, 54.1, 372.2, 44; 524/704; 264/4.33, 4.7

[56] References Cited

U.S. PATENT DOCUMENTS 3,955,012 5/1976 Okanura et al. ...................... 424/36
3,962,416 6/1976 Katzen ................................. 424/19

Primary Examiner—Howard S. Williams
Attorney, Agent, or Firm—Browdy and Neimark

[57] ABSTRACT

A process is, herein disclosed, for producing a slow release composite having a physiologically active substance encapsulated therein, which comprises preparing a system wherein one or more physiologically active substances are in contact with protein from one or more protein sources, and bringing said system into direct contact with steam at temperatures between 50° C. and 100° C. to denature the protein and make the same hydrophobic, to thereby make a slow release composite having the physiologically active substance dispersed, fixed and encapsulated therein. And a process is also disclosed for producing a slow release composite which comprises preparing a mixture of one or more hydrophilic polymerizable monomers containing the body fluid and/or isotonic solution, protein from one or more protein sources, and one or more physiologically active substances, subjecting the mixture to direct contact with steam and irradiation with light or ionizing radiation, said treatment with steam being performed either before or simultaneously with irradiation with light or ionizing radiation.

1 Claim, 15 Drawing Figures

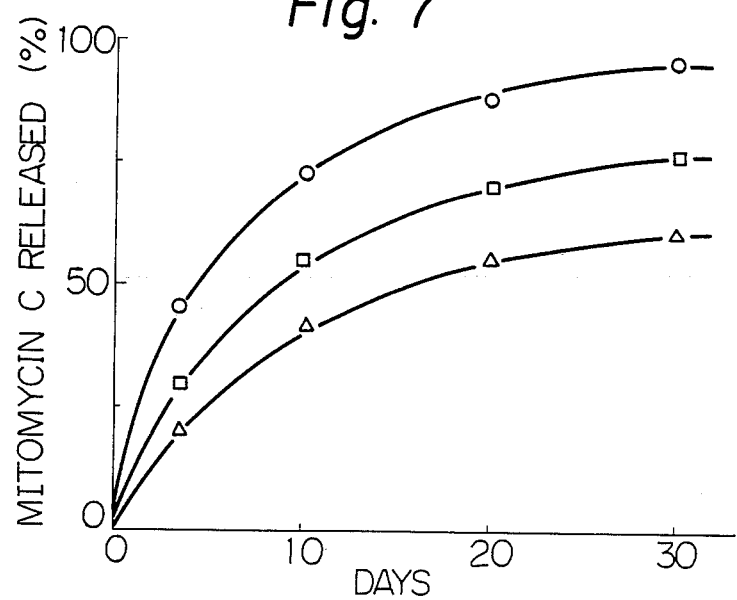
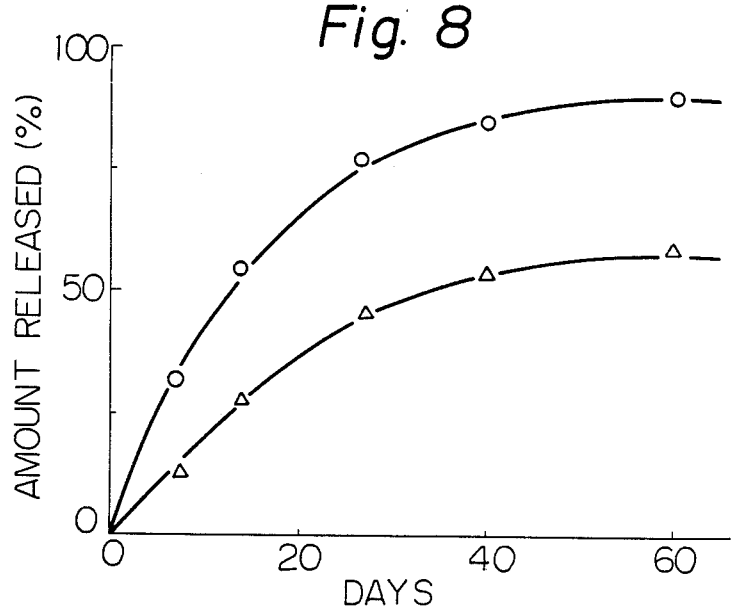

PROCESS FOR PRODUCING A SLOW RELEASE COMPOSITE

RELATED APPLICATION

This is a continuation-in-part application of U.S. patent application Ser. No. 233,084 filed Feb. 10, 1981, now abandoned.

BACKGROUND OF THE INVENTION

1. Field of the Invention

This invention relates to a process for producing a slow release composite having a physiologically active substance encapsulated therein, which comprises preparing a system wherein one or more physiologically active substances are in contact with protein from one or more protein sources, and bringing said system into direct contact with steam at temperatures between 50° C. and 100° C. to denature the protein and make the same hydrophobic, to thereby make a slow release composite having the physiologically active substance dispersed, fixed and encapsulated therein. And this invention also relates to a process for producing a slow release composite which comprises preparing a mixture of one or more hydrophilic polymerizable monomers containing body fluid and/or isotonic solution, protein from one or more protein sources, and one or more physiologically active substances, and bringing said mixture into direct contact with steam at temperatures between 50° C. and 100° C. and irradiating with light or ionizing radiation, said contact with steam being performed either before or simultaneously with irradiation with light or ionizing radiation.

DESCRIPTION OF THE PRIOR ART

Farhadieh et al U.S. Pat. No. 3,922,379 discloses a process for protecting particles of substantially water-insoluble, pharmaceutically active, erythromycin derivatives from being inactivated by the acids of the stomach and simultaneously to cover their objectionable taste. However, Farhadieh et al do not use "direct contact with steam" as means for denaturation of protein.

Okamura et al U.S. Pat. No. 3,955,012 discloses that medical articles composed of silicone rubber coated with collagen to be used in living body are manufactured by subjecting a surface of shaped articles composed of silicone rubber to a spark discharge, coating the thus treated surface with an acidic aqueous solution of collagen and then drying said surface to form collagen layer and irradiating the shaped article coated with collagen with high energy ionizing radiation under an atmosphere having such a humidity that the water content of the coated collagen becomes more than 20% by weight. Okamura et al do not disclose or suggest that collagen is brought into direct contact with steam at relatively high temperatures between 50° C. and 100° C. which is one of the most significant features of this invention.

Katzen U.S. Pat. No. 3,962,416 discloses the technical concept of drying gelatinized encapsulating agent by flashing off the entrapped water as steam and does not disclose or suggest the denaturation of the protein by contacting directly with steam at temperatures between 50° C. and 100° C. which is one of the most significant feature of this invention.

Yapel U.S. Pat. No. 4,147,767 discloses solid serum albumin spherules having 5 to 30 percent by weight of an organic modicament homogeneously entrapped therein. Yapel does not use or suggest the denaturation of serum albumin by contacting directly with steam at temperatures between 50° C. and 100° C.

SUMMARY OF THE INVENTION

An object of this invention is to provide a process for producing a slow release composite having a physiologically active substance.

Another object of this invention is to provide a process for producing a slow release composite wherein a physiologically active substance is supported on protein in such a manner that the efficacy of the active substance is sustained for a significantly prolonged period of time.

Further object of this invention is to provide a process for producing a slow release composite having a physiologically active substance encapsulated therein, which comprises preparing a system wherein one or more physiologically active substances are in contact with protein from one or more protein sources, and bringing said system into direct contact with steam at temperatures between 50° C. and 100° C. to denature the protein and make the same hydrophobic, to thereby provide a chemical treatment whereby a slow release composite is produced having the physiologically active substance dispersed, fixed and encapsulated therein.

Another object of this invention is to provide a process for producing a slow release composite which comprises preparing a mixture of one or more hydrophilic polymerizable monomers containing the body fluid and/or isotonic solution, protein from one or more protein sources, and one or more physiologically active substances, and bringing said mixture into direct contact with steam at temperatures between 50° C. and 100° C. and irradiating with light or ionizing radiation, said contact with steam being performed either before or simultaneously with irradiation with light or ionizing radiation.

Other objects and advantages of this invention will be apparent to those skilled in the art from a consideration of the description of this invention.

BRIEF DESCRIPTION OF THE DRAWINGS

FIGS. 1 to 14 are graphs depicting the results of tests conducted to see how various physiologically active substances were released from the slow releasing composites produced according to the process of this invention.

DETAILED DESCRIPTION OF THE INVENTION

Figure 1:
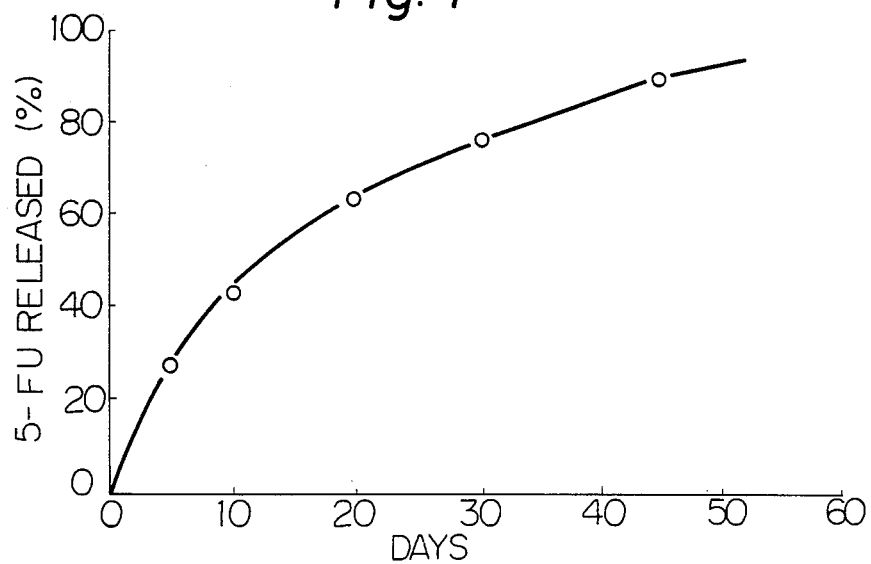

This invention provides a process for producing a slow release composite having a physiologically active substance encapsulated therein. The process comprises preparing a system wherein one or more physiologically active substances are in contact with protein from one or more protein sources, bringing said system into direct contact with steam at temperatures between 50° C. and 100° C. to denature the protein and make the same hydrophobic, to thereby make a slow release composite having the physiologically active substance dispersed, fixed and encapsulated therein.

The resulting slow release composite can be used as a core to make a two-layered slow release composite by forming another slow release composite around the core. For this purpose, the core is brought into contact with a system comprising one or more physiologically active substances and protein from one or more protein sources, and while they are kept in contact, they are subjected to a physical and/or chemical treatment to thereby denature the protein. If desired, a multilayered slow release composite can be prepared by repeating the above procedure.

In the practice of this invention, protein is brought into contact with a physiologically active substance in liquid or solid phase. For contact in liquid phase, a system wherein one or more physiologically active substances are in contact with an aqueous solution of protein from one or more protein sources is subjected to a direct contact with steam at temperatures between 50° C. and 100° C. to denature the protein and make the same hydrophobic, to provide a slow release composite wherein the physiologically active substance is dispersed, fixed or encapsulated in denatured. In this case, 0.1 to 500 parts by weight of a 0.1 to 50 wt. % aqueous protein solution is suitably used on the basis of 1 to 100 parts by weight of the physiologically active substance. For contact in solid phase, the powder of one or more physiologically active substances is thoroughly mixed with the powder of protein from one or more protein sources, the mixture is pressed into a desired shape, the mixture is then subjected to a direct contact with steam at temperature between 50° C. and 100° C. to denature the protein and make the same hydrophobic, to provide a slow release composite wherein the physiologically active substance is encapsulated in denatured matrix. The slow releasability of the physiologically active substance is further improved by irradiating the resulting composite with light or ionizing radiation. For contacting the physiologically active substance and protein in solid phase, 0.1 to 500 parts by weight of 0.1 to 50 wt. % protein is suitably used on the basis of 1 to 100 parts by weight of the physiologically active substance.

One feature of this invention is to physically and/or chemically denature protein that is used as a matrix within which the physiologically active substance is encapsulated. Physical means to denature protein include heat treatment, pressure application, irradiation with ultraviolet rays, X-rays, application of sound waves, shaking, and freezing. Chemical means include addition of chemicals such as acid, base, acetone, alcohol, and surfactant. Some of the changes that occur as a result of protein denaturation are reduced solubility, loss of crystallinity, and change in molecular weight and formula. As mentioned above, protein can be denatured by many different methods, and natural protein is generally considered to have been "denatured" when it has been changed by one of the techniques specified above. Although there is no established definition of the mechanism of protein denaturation, for the purposes of this invention, protein is regarded as "denatured" if it is coagulated in such a manner that it has a physiologically active substance dispersed, fixed or encapsulated therein.

One of the most significant feature of this invention is to employ a direct contact with steam at a relatively high temperature between 50° C. and 100° C.

That is to say, a system, wherein one or more physiologically active substances are in contact with a protein from one or more protein sources, is brought into direct contact with steam at temperatures between 50° C. and 100° C. This treatment causes protein denaturation and the protein turns more hydrophobic (its water absorption is decreased). It is essential for the purpose of the present invention to bring protein into direct contact with steam and heat it at temperatures between 50° C. to 100° C. Only when these two requirements are met is the hydrophilicity of protein greatly reduced and the period over which the active ingredient is released extended. Heating in the absence of steam is ineffective. Even in the presence of steam, heating at temperatures below 50° C. is not sufficient to attain object of this invention.

The basic concept of the method of this invention has been described above. The invention also includes a method for producing a slow release composite that contains a physiologically active substance having improved slow releasability. The method comprises preparing a mixture of 10 parts by weight of one or more hydrophilic polymerizable monomers containing 0.1 to 95% body fluid and/or isotonic solution, 1 to 500 parts by weight of thermally denaturable protein from one or more protein sources, and 1 to 1000 parts by weight of one or more physiologically active substances, and subjecting the mixture direct contact with steam at temperatures between 50° C. and 100° C. simultaneously with, or followed by, irradiation with light or ionizing radiation. The primary object of this modified method is to further prolong the slow release of the physiologically active substance by supporting it on thermally denatured protein and a polymer of the hydrophilic polymerizable monomer.

The body fluid used in the modified method means the fluid within the living organism, and is illustrated by blood plasma, interstitial fluid, lymph fluid, secretions, tears, and milk. The isotonic solution is a solution having an osmotic pressure equal to the physiological osmotic pressure and it is illustrated by isotonic sodium chloride solution, Ringer's solution, Locke's solution and 5% glucose injection solution. These body fluids or isotonic solutions take part in protein denaturation in the modified method of this invention.

Examples of the hydrophilic polymerizable monomer compatible with the living organism that is used in the modified method include 2-hydroxyethyl methacrylate, hydroxyethyl acrylate, acrylamide, N-vinyl-2-pyrrolidone, and dimethylaminoethyl methacrylate.

Examples of the physiologically active substance that are used in the method of this invention include bleomycin hydrochloride, mitomycin C, adriamycin, carbazyl quinone, rhomstin, diphosphamide, thioinosine, citarabin, fluorouracil, 1-(2-tetrahydrofuryl)-5-fluorouracil, citoteine, chlorambutyl, bibromomannitol, thio-TEPA, cyclophosphamide, acetylurin, noradrenaline, serotonin, callicrein, gastrin, secretin, adrenaline, insulink glucagon, β-methazone, indometasine, ACTH, growth hormone, gonadotrophin, oxytocin, vasopressin, thyroxine, testicular hormone, vesicular hormone, luteal hormone, adrenal cortical hormone, prostaglandin, antihistamics, hypotensive agents, vasoconstrictor, capillary stabilizer, stomachic/digestives, intestinal control agents, contraceptives, dermatologic bacteriocide/disinfectants, agents for treating parasitic dermal diseases, antiinflammatories, vitamins, enzyme preparations, vaccines, antiprotozoan agent, interferon inducing substances, antehelmintics agents, for treating fish diseases, agrichemicals, auxins gibberellins, cidocainine, abietic acid, insect hormones, etc.

The protein used in this invention is derived from various sources such as beta-globulin, gamma-globulin, albumen albumin, milk albumin, bovine serum albumin, human serum albumin, other serum albumins, human serum globulin, leucosin, hemoglobin, globin, collagen, gelatin, alpha-lipoprotein, beta-lipoprotein, fibrinogen, ovoalbumin, conalbumin, casein, euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, and elastin.

Protein can also be denatured by irradiation with light or ionizing radiation. The light includes visible and ultra-violet rays from various sources, and optionally, a photosensitizer may be used. Examples of the ionizing radiation include alpha-, beta- and gamma-rays for radioactive isotopes, fission products, and nuclear reactors or the like, accelerated neutron rays and mixed radiations and electron beams from accelerators. A suitable dose rate is in the range of from $1 \times 10^2$ to $1 \times 10^9$ roentgens/hr. and a suitable total dose to be given is in the range of from $1 \times 10^3$ to $1 \times 10^7$ roentgens.

This invention is now described in greater detail by reference to the following examples and comparative examples which are given here for illustrative purposes only and are by no means intended to limit the scope of the invention. In the examples, tests were conducted to see how various physiologically active substances in the slow release composite dissolved into 1000 ml of water. The tests were conducted in accordance with USP XIX at 37° C. with a basket rotating at 100 rpm.

EXAMPLE 1

Water (10 ml) of water was added to a mixture of 500 mg of 5-fluorouracil (5-FU) and 500 mg of bovin serum albumin in a glass ampule, and they were mixed under stirring. The ampule was heated at 100° C. for 5 seconds to shrink and denature albumin with steam generated in the ampule. A hard bar of thermally denatured albumin containing 5-fluorouracil resulted. A test was conducted to see how 5-fluorouracil was released from the bar in vitro. The release profile is shown in FIG. 1.

EXAMPLE 2

Figure 2:
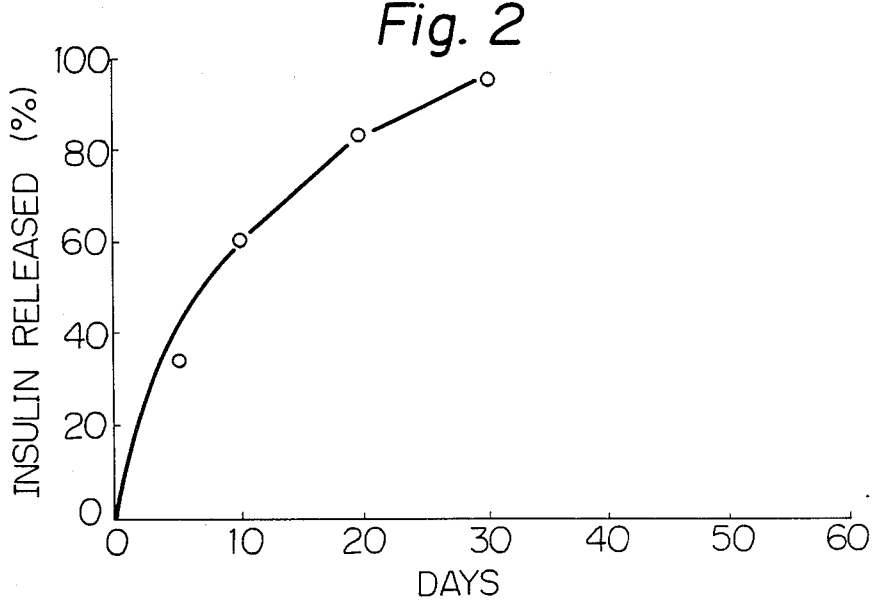

Water (5 ml) was added to a mixture of 100 mg of insulin and 100 mg of gamma-globulin in an ampule, and they were mixed under stirring. The resulting mixture was freeze-dried, taken out of the ampule and put in a hot bath (90° C.) to shrink and denature gamma-globulin by steam generated in the ampule. A hard tablet of thermally denatured gamma-albumin containing insulin resulted. A test was conducted to see how insulin was released from the tablet in vitro. The release profile is shown in FIG. 2.

EXAMPLE 3

Figure 3:
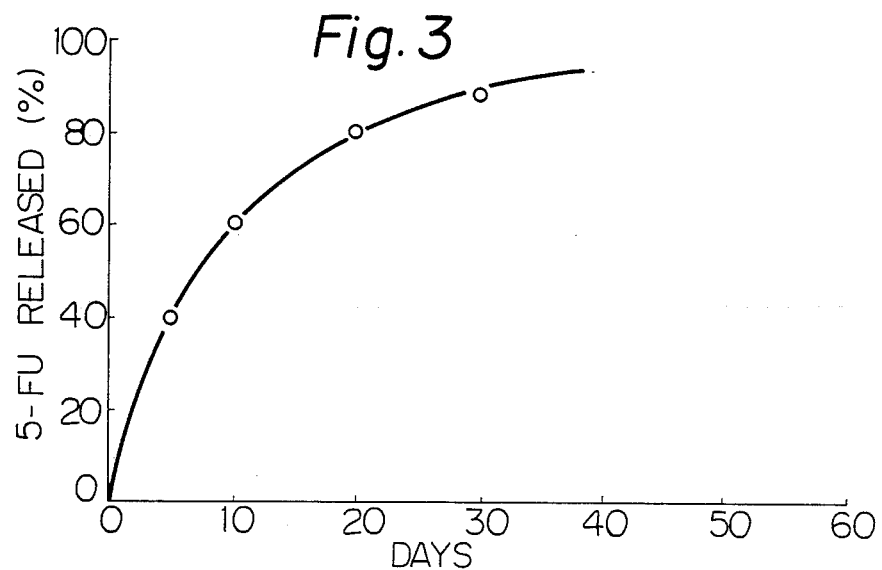

Water (10 ml) was added to a mixture of 500 mg of 5-fluorouracil and 500 mg of a mixture of 70% albumin and 30% gelatin in a glass ampule, and they were mixed under stirring. The resulting mixture was shrunk and denatured in the same manner as in Example 1. A hard bar of thermally denatured protein containing 5-fluorouracil resulted. A test was conducted to see how 5-fluorouracil was released from the bar in vitro. The release profile is depicted in FIG. 3.

EXAMPLE 4

Figure 4:
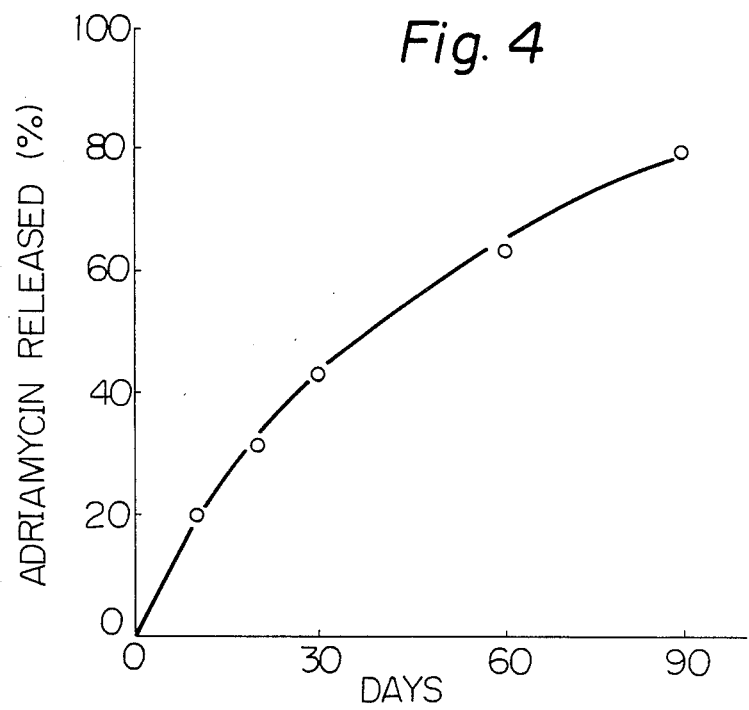

Water (5 ml) was added to a mixture of 50 mg of adriamycin (ADM) and 200 mg of human serum albumin in a glass ampule, and they were mixed under stirring. The ampule was put in a hot bath (90° C.) for one minute to shrink and denature albumin with steam generated in the ampule. A hard tablet (14 mm$\phi$) of thermally denatured albumin containing adriamycin resulted. A test was conducted to see how adriamycin was released from the tablet in vitro. The release profile is depicted in FIG. 4.

EXAMPLE 5

Figure 5:
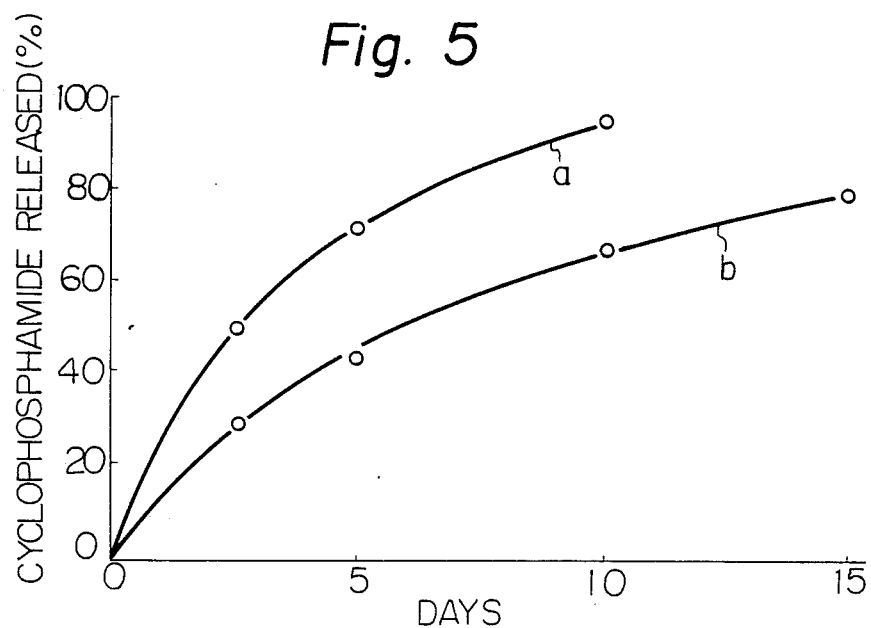

Water (10 ml) was added to a mixture of 500 mg of cyclophosphamide and 500 mg of human serum albumin in a glass ampule, and they were mixed under stirring. The ampule was left to stand in a hot bath (100° C.) for 3 minutes to shrink and denature albumin with hot steam generated in the ampule. The mixture was removed from the ampule and dried with air. A bar of thermally denatured albumin containing cyclophosphamide resulted. A test was conducted to see how cyclophosphamide was released from the bar in vitro. The release profile is depicted by the solid line a in FIG. 5.

EXAMPLE 6

A glass ampule containing the mixture of denatured albumin and cyclophosphamide prepared in Example 5 was purged with nitrogen gas, fused, and irradiated at room temperature with gamma-rays from Co-60 at a dose rate of $5 \times 10^5$R/hr for one hour. A bar of thermally denatured albumin containing cyclophosphamide resulted. A test was conducted to see how albumin was released from the bar in vitro. The release profile is depicted by the solid line b in FIG. 5.

EXAMPLE 7

Figure 6:
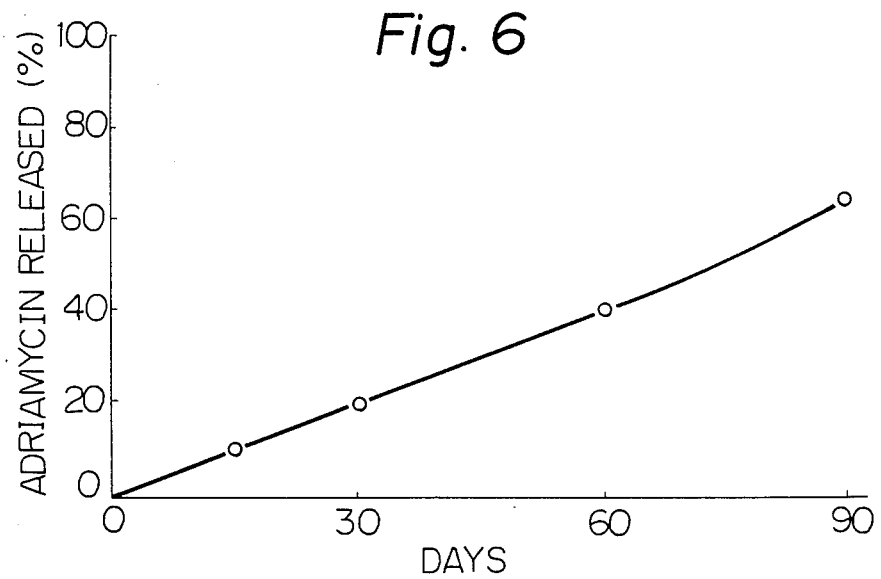

Water (2 ml) was added to a mixture of 50 mg of ADM and 50 mg of human serum albumin in a glass ampule, and they were mixed under stirring. The ampule was left to stand in a hot bath (90° C.) for 30 seconds to shrink and denature albumin with steam generated in the ampule. The mixture was put in the middle of another mixture of 200 mg of human serum albumin, 10 mg of ADM and 5 ml of water in a glass ampule, and left to stand in a hot bath (50° C.) for one minute to shrink and denature albumin with heat. The mixture was then removed from the ampule and dried with air. A bar of thermally denatured albumin containing ADM resulted. A test was conducted to see how albumin was released from the bar. The release profile is depicted in FIG. 6.

EXAMPLE 8

The sample prepared in Example 7 was planted under the skin of a group of ICR female mice in the backs of which skin cancer had been developed. All mice of a control group died of skin cancer in one month, but 60% of the treated mice were still alive when one year had passed, indicating the great life extending effect of the sample prepared in Example 7. The weight of the sample recovered from the living mice was a sixth of the initial weight, and there was no sign of rejection taking place around the tissues of the site where the sample was planted.

EXAMPLE 9

An MMC powder (40 mg) was mixed thoroughly with 10 mg of a human serum albumin powder by a mechanical means. The resulting mixture was pressed at 200 kg/cm$^2$ into pellets 10 mm in diameter which were steamed at 80° C. to cause thermal denaturation of albumin. A test was conducted to see how MMC was released from the pellets in vitro. The release profile is shown by the line in FIG. 7.

EXAMPLE 10

The procedure of Example 9 was repeated except that the MMC powder was mixed with 50 mg of a human serum albumin powder. The release profile is shown by the line □ in FIG. 7.

EXAMPLE 11

The procedure of Example 10 was repeated except that the MMC powder was mixed with 100 mg of a human serum albumin powder. The release profile is shown by the line Δ in FIG. 7.

EXAMPLE 12

A bleomycin (BLM) powder (100 mg), 500 mg of 5-fluorouracil (5-FU) and 400 mg of a bovine serum albumin powder were mixed thoroughly by a mechanical means. The resulting mixture was pressed at 200 kg/cm$^2$ into a bar of 7 mm in diameter which was steamed at 50° C. for thermal denaturation of albumin. A test was conducted to see how BLM and 5-FU were released from the bar in vitro. The release profile is depicted in FIG. 8 by the line for 5-FU and by the line Δ for BLM.

EXAMPLE 13

The bar prepared in Example 12 was irradiated in a nitrogen atmosphere with gamma-rays for Co-60 to give a total dose of $1 \times 10^6$ R. A test was conducted to see how BLM and 5-FU were released from the bar in vitro: 70% of 5-FU was released in 60 days, and more than 95% released in 90 days, whereas 45% of BLM was released in 60 days and 79% released in 90 days.

EXAMPLE 14

The sample prepared in Example 10 was planted intraperitoneally in a group of ICR female mice in which Ehrlich ascites tumor cells were trasplanted. All mice of a control group died of ascites cancer in about 15 days, but 75% of the treated mice were still alive when seven months had passed, indicating the great life extending effect of the sample prepared in Example 10. There was little sample left in the tissues of the site where the sample was planted, and no sign of rejection was found around those tissues. EXAMPLE 15

Figure 9:
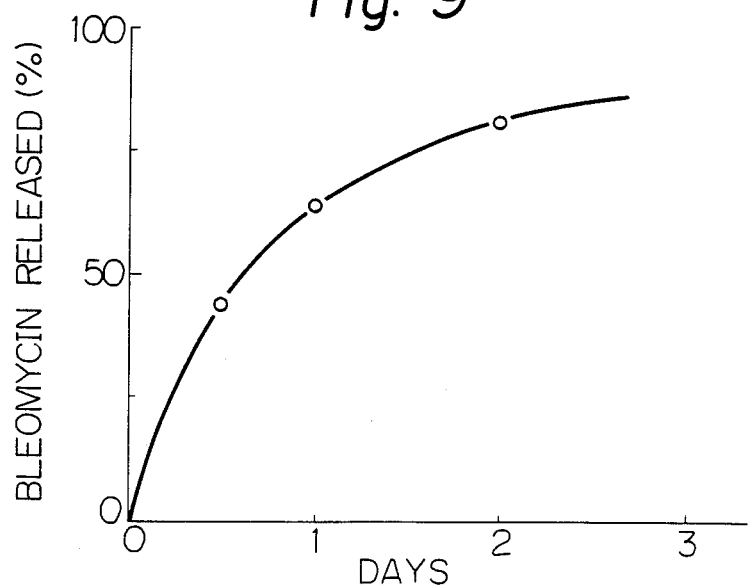

Water (1 ml) was added to a mixture of 200 mg of soluble collagen and 40 mg of bleomycin (BLM) in a glass ampule, and they were mixed thoroughly under stirring. The resulting mixture was irradiated with $5 \times 10^5$ rad. of gamma-rays from Co-60, freeze-dried and taken out of the ampule. A soft bar of slow release composite resulted. A test was conducted to see how BLM was released from the bar in vitro. The release profile is depicted in FIG. 9.

EXAMPLE 16

Figure 10:
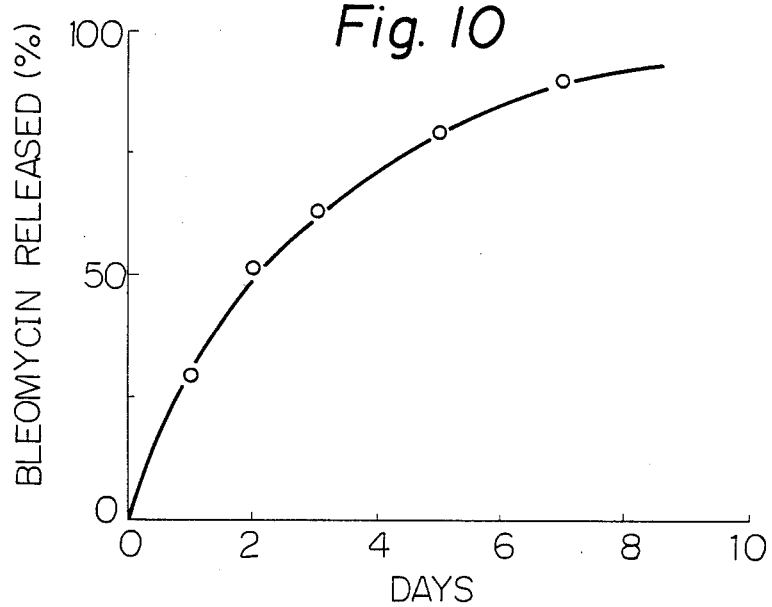

Water (1 ml) was added to a mixture of 300 mg of soluble collagen and 50 mg of BLM in a glass ampule, and they were mixed under stirring. The resulting mixture was placed in a hot bath (100° C.) for 5 minutes to denature BLM with heat steam generated in the ampule. The mixture was then irradiated in a nitrogen atmosphere with 1 M rad. of electron beams, and freeze-dried. A hard bar of slow release composite resulted. A test was conducted to see how BLM was released from the bar in vitro. The release profile is depicted in FIG. 10.

EXAMPLE 17

Figure 11:
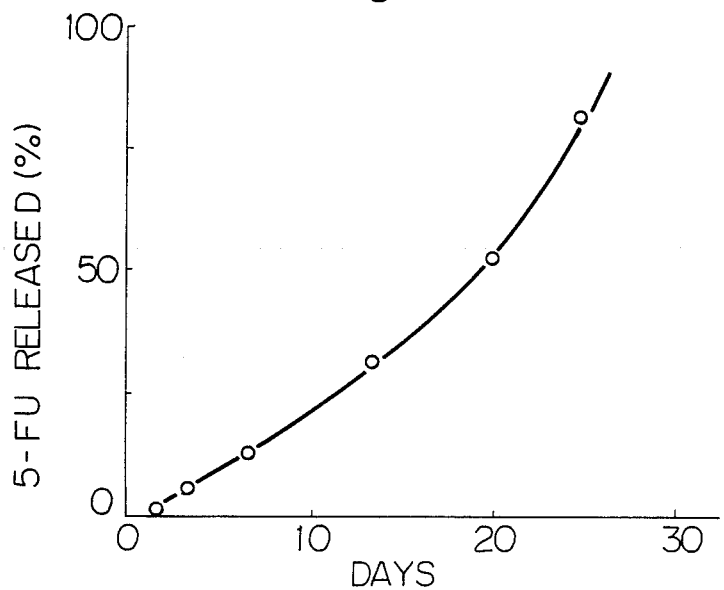

A solution of 300 mg of soluble collagen in 1 ml of water was prepared in a glass ampule. The bar of slow release composite prepared in Example 16 was put in the middle of the solution, heated at 60° C., and freeze-dried. A bar of two-layered slow release composite resulted. A test was conducted to see how BLM was released from the bar in vitro. The release profile is depicted in FIG. 11.

EXAMPLE 18

Figure 12:
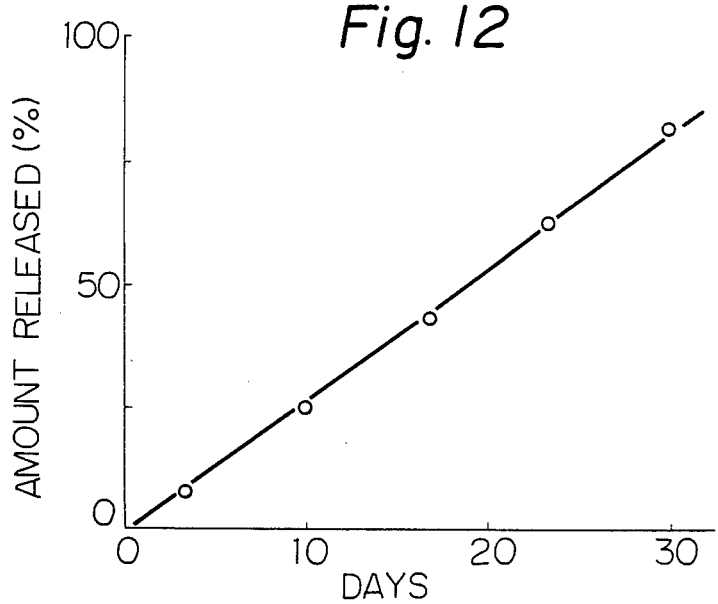

Water (1 ml) was added to a mixture of 300 mg of soluble collagen and 30 mg of BLM in a glass ampule, and they were mixed under stirring. The bar of slow release composite prepared in Example 16 was put in the middle of the resulting mixture, heated at 70° C., irradiated with $1 \times 10^6$ rad. of gamma-rays from Co-60, and freeze-dried. A hard bar of two-layered slow release composite resulted. A test was conducted to see how BLM was released from the bar in vitro. The release profile is depicted in FIG. 12.

EXAMPLE 19

The sample prepared in Example 18 was planted intraperitoneally in a group of ICR female mice in which Ehrlich ascites tumor cells were transplanted. All mice of a control group died of ascites cancer in about 10 days, but 70% of the treated mice were still alive when eight months had passed, indicating the great life extending effect of the sample prepared in Example 18. The size of the sample recovered from the living mice was tenth of the initial size, and there was no sign of rejection taking place around the tissues of the site where the sample was planted.

EXAMPLE 20

Figure 13:
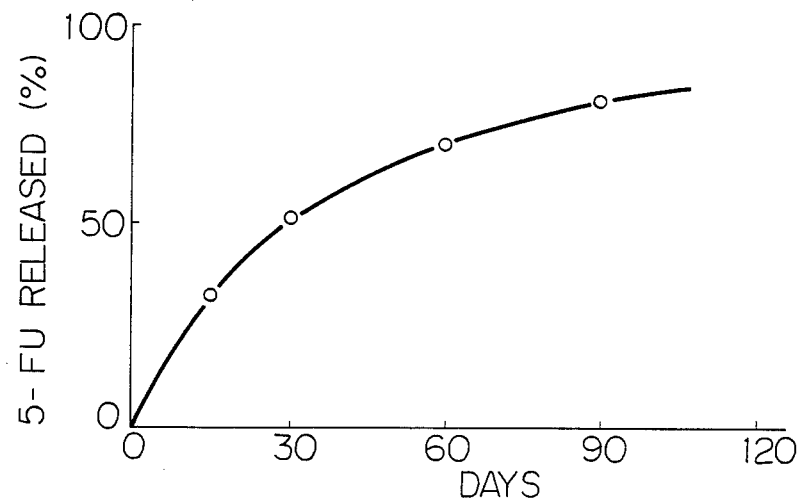

Isotonic sodium chloride solution (1 ml) containing 40% 2-hydroxyethyl methacrylate was mixed with 1 g of human serum albumin and 500 mg of 5-fluorouracil (5-FU), and the mixture was heated at 70° C. and irradiated with 1 Mrad of gamma-rays from Co-60 at $-78°$ C. A hard bar (8mmφ) of slow release composite resulted. A test was conducted to see how 5-FU was released from the bar in vitro. The release profile is depicted in FIG. 13. The bar was planted in the back of ICR female mice, and when it was recovered 2 years later, its weight was 10% of the initial weight, indicating 90% of it was consumed. The compound was highly compatible with the surrounding tissues, producing no tumor or other neoplasms at all.

EXAMPLE 21

A bar of slow release composite was prepared by repeating the procedure of Example 20 except that the mixture irradiated with gamma-rays from Co-60 was subsequently heat-treated. The performance of the bar was comparable to or higher than that of the sample prepared in Example 21.

EXAMPLE 22

A bar of slow release composite was prepared by repeating the procedure of Example 20 except that the mixture was steamed at 60° C. while it was irradiated with 0.8 Mrad. of electron beams from an accelerator. The performance of the bar was comparable to or higher than that of the sample prepared in Example 20.

EXAMPLE 23

Figure 14:
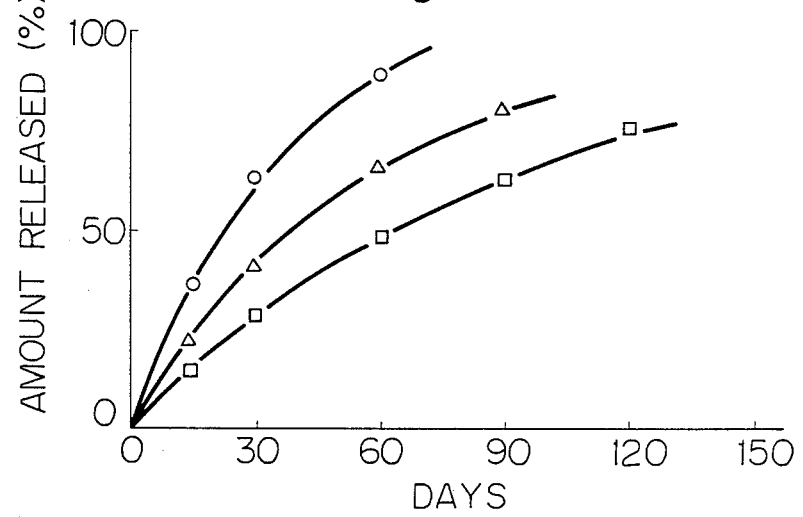

Isotonic sodium chloride solution (1 ml) containing 50% polymerizable monomer (i.e. a mixture of 50% hydroxyethyl acrylate and 50% diethylaminoethyl methacrylate) was mixed with 1 g of 50% protein (i.e. a mixture of 50% human serum albumin and 50% Bact-hemoglobin), 100 mg of bleomycin (BLM), 100 mg of adriamycin (ADM) and 400 mg of 5-FU. The resulting mixture was irradiated with 1.5 Mrad. of gamma-rays from Co-60 at −78° C., and steamed at 75° C. A test was conducted to see how the respective antitumor agents were released from the resulting slow release composite. The release profile is depicted in FIG. 14 wherein the initial amount of each antitumor agent is 100%: in the figure, - -, -Δ- and -□- indicate 5-FU, ADM and BLM, respectively. The composite was planted in the back of ICR female mice, and when it was recovered after six months its weight was 30% of the initial weight. The composite was highly compatible with the surrounding tissues, producing no tumor or other neoplasms at all.

REFERENCE EXAMPLE

1. Object

The most significant object of this invention is to provide a process for producing a slow release composite having a physiologically active substance encapsulated therein. To attain this object, a system wherein one or more physiologically active substances are in contact with a protein in first prepared.

Then, the system is heated with steam (which contacts and is absorbed by the system) at temperatures between 50° C. and 100° C. This treatment with steam causes protein denaturation and the protein turns more hydrophobic (its water absorption is decreased). It is essential for the purpose of this invention to bring protein into contact with steam and heat it at temperatures between 50° C. and 100° C. Only when these two requirements are met is the hydrophilicity of protein greatly reduced and the period over which the active ingredient is released extended. Heating in the absence of water is ineffective. Even in the presence of water, heating at for example, 40° C. is not sufficient to attain an object of this invention. To demonstrate this point, the following experiments were conducted.

2. Experiments

2-1: Experiment 1

Figure 15:
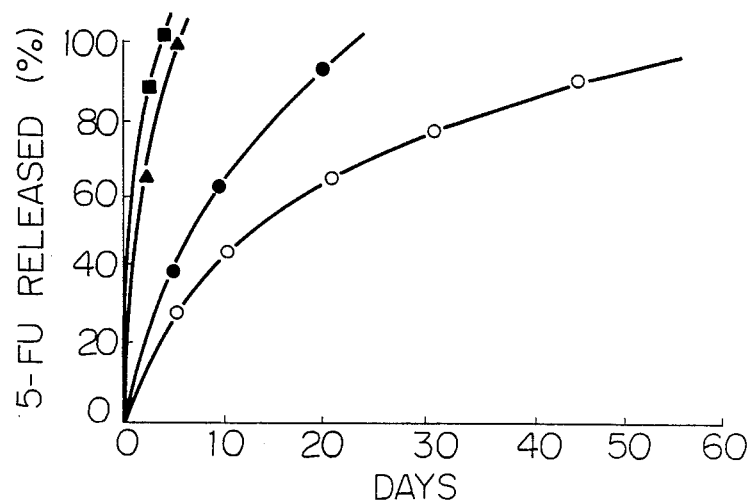
FIG. 15 is a graph showing the effects of heating temperature of protein on the release profile of physiologically active substance from the slow releasing composite.

Water (10 ml) was added to a mixture of 500 mg of 5-fluorouracil (5-FU) and 500 mg of bovine serum albumin in a glass ampule, and they were mixed under stirring. The ampule was then put in a hot bath (100° C.) for 5 seconds to shrink and denature albumin with steam generated in the ampule. A hard bar of denatured albumin containing 5-FU resulted. A test was conducted to see how 5-FU was released from the bar in vitro. The release profile is depicted in the accompanying FIG. 15 (curve 0).

2-2: Experiment 2–4

The procedure of Experiment 1 was repeated except that the bath temperature was set at 50° C., 40° C. and 30° C. The profile of release of 5-FU from albumin is depicted in accompanying Fig., wherein curves , Δ and □ indicate the results at 50° C., 40° C. and 30° C., respectively.

2-3: Experiment 5

The procedure of Example 1 was repeated except that the bath temperature was varied from 30° C. to 90° C. by 10° C. The following table shows how the water absorption of denatured albumin changed with temperature.

| temp. (°C.) | 30 | 40 | 50 | 60 | 70 | 80 | 90 |
|---|---|---|---|---|---|---|---|
| water absorption (%) | 65.8 | 61.2 | 34.2 | 22.9 | 8.4 | 6.9 | 6.7 |

II. Conclusion

From the results obtained by the Experiments 1–4, it should be concluded that the period over which the physiologically active substance (5-fluorouracil) is released from protein thermally denatured at temperatures 50° C. and 80° C. is significantly prolonged compared with those from protein thermally denatured at temperatures 40° C. and 30° C.

We claim:

1. A process for producing a slow release composite which comprises preparing a mixture of one or more hydrophilic polymerizable monomers containing body fluid and/or isotonic solution, protein from one or more protein sources, and one or more physiologically active substances, and bringing said mixture into direct contact with steam at temperatures between 50° C. and 100° C. and irradiating with light or ionizing radiation, said contact with steam being performed either before or simultaneously with irradiation with light or ionizing radiation.

* * * * *